US009468759B2

(12) United States Patent
Escribano

(10) Patent No.: US 9,468,759 B2
(45) Date of Patent: *Oct. 18, 2016

(54) ELECTROKINETIC NERVE STIMULATOR

(71) Applicant: Kato Medical Systems, LLC, Seattle, WA (US)

(72) Inventor: Rafael Escribano, Tacoma, WA (US)

(73) Assignee: Kato Medical Systems, LLC, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/684,176

(22) Filed: Apr. 10, 2015

(65) Prior Publication Data

US 2015/0209584 A1    Jul. 30, 2015

Related U.S. Application Data

(63) Continuation of application No. 13/343,251, filed on Jan. 4, 2012, now Pat. No. 9,114,258.

(60) Provisional application No. 61/429,683, filed on Jan. 4, 2011.

(51) Int. Cl.
| | |
|---|---|
| *A61N 1/00* | (2006.01) |
| *A61N 1/36* | (2006.01) |
| *A61N 1/04* | (2006.01) |
| *A61K 31/4178* | (2006.01) |
| *A61K 31/573* | (2006.01) |
| *A61M 37/00* | (2006.01) |

(52) U.S. Cl.
CPC ....... *A61N 1/36025* (2013.01); *A61K 31/4178* (2013.01); *A61K 31/573* (2013.01); *A61N 1/0456* (2013.01); *A61N 1/0492* (2013.01); *A61N 1/3606* (2013.01); *A61N 1/36007* (2013.01); *A61M 37/00* (2013.01)

(58) Field of Classification Search
CPC .......... A61K 31/4178; A61K 31/573; A61M 37/00; A61N 1/0456; A61N 1/0492; A61N 1/36007; A61N 1/36025; A61N 1/3606
See application file for complete search history.

(56) References Cited

U.S. PATENT DOCUMENTS

| | | | |
|---|---|---|---|
| 4,559,222 A | 12/1985 | Enscore et al. | |
| 4,981,146 A | 1/1991 | Bertolucci | |
| 5,397,338 A | 3/1995 | Grey | |
| 5,496,266 A * | 3/1996 | Haak et al. | ..... 604/20 |
| 5,733,255 A | 3/1998 | Dinh et al. | |
| 6,021,348 A | 2/2000 | James | |

(Continued)

FOREIGN PATENT DOCUMENTS

WO    WO9415668    7/1994

OTHER PUBLICATIONS

Amberger, Michael, M.D., et al., "Monitoring of Neuromuscular Blockade at the P6 Acupuncture Point Reduces the Incidence of Postoperative Nausea and Vomiting", Anesthesiology, V. 107, No. 6, Dec. 2007, pp. 903-907.

(Continued)

*Primary Examiner* — George Manuel
(74) *Attorney, Agent, or Firm* — Steptoe & Johnson LLP

(57) ABSTRACT

A device and method for stimulating nerves. In one application, the approaches treat nausea and vomiting caused by a reaction to general anesthesia. A bi-modal approach involving acustimulation and medicants is contemplated for specific conditions.

9 Claims, 2 Drawing Sheets

(56) References Cited

U.S. PATENT DOCUMENTS

| | | |
|---|---|---|
| 6,076,018 A | 6/2000 | Sturman |
| 6,135,953 A | 10/2000 | Carim |
| 6,226,552 B1 | 5/2001 | Staunton et al. |
| 6,375,990 B1 | 4/2002 | Nemeroff et al. |
| 6,493,588 B1 | 12/2002 | Malaney et al. |
| 6,961,622 B2 | 11/2005 | Gilbert |
| 7,171,276 B2 | 1/2007 | Giuntoli |
| 7,200,444 B2 | 4/2007 | Gavronsky et al. |
| 7,283,874 B2 | 10/2007 | Penner |
| 7,613,517 B2 * | 11/2009 | Goroszeniuk .................. 607/46 |
| 7,643,874 B2 | 1/2010 | Nitzan et al. |
| 7,728,042 B2 | 6/2010 | Eros et al. |
| 2002/0193844 A1 | 12/2002 | Michelson et al. |
| 2003/0069627 A1 | 4/2003 | Giuntoli et al. |
| 2005/0085751 A1 | 4/2005 | Daskal et al. |
| 2005/0181341 A1 | 8/2005 | Ewing et al. |
| 2006/0041283 A1 | 2/2006 | Gelfand et al. |
| 2007/0088419 A1 | 4/2007 | Fiorina et al. |
| 2009/0182393 A1 * | 7/2009 | Bachinski .......... A61N 1/37264 607/59 |

OTHER PUBLICATIONS

Tang, Jun, M.D., et al., "The Effect of Timing of Ondansetron Administration on Its Efficacy, Cost-Effectiveness, and Cost-Benefit as a Prophylactic Antiemetic in the Ambulatory Setting", Anesth Analg 1998;86:274-282.

Zarate, Eduardo, M.D., et al., "The Use of Transcutaneous Acupoint Electrical Stimulation for Preventing Nausea and Vomiting After Laparoscopic Surgery", Anesth Analg 2001;92:629-635.

Aetna.com Clinical Policy Bulletin: Electrical Stimulation for Nausea, Vomiting and Motion Sickness (PrimaBella and ReliefBand), Mar. 12, 2010, No. 0676.

Nerve and muscle stimulators "on sale" by LGMedSupply.com, 5 pages printed Aug. 28, 2008. http://www.lgmedsupply.com/tensproducts.html.

Nerve and muscle stimulators "on sale" by Medical Products Online, Inc., 1 page printed Aug. 28, 2008. http://www.medicalproductsonline.org/electrotherapy2.html.

* cited by examiner

ELECTROKINETIC NERVE STIMULATOR

CROSS-REFERENCES TO RELATED APPLICATIONS

This application is a continuation of U.S. application Ser. No. 13/343,251, filed Jan. 4, 2012, which claims the benefit of Provisional Application Ser. No. 61/429,683, filed Jan. 4, 2011, the contents of which are incorporated by reference.

BACKGROUND OF THE INVENTION

The present disclosure is directed towards devices and methods for stimulating nerves. In one application, an approach for more effectively treating post-surgical symptoms is contemplated.

A common side effect of surgery is nausea and vomiting caused by a reaction to the general anesthetic. In fact, nausea, vomiting, and retching after surgical procedures not only cause patient discomfort, but can also prolong time to discharge from ambulatory surgery centers and results in unanticipated hospital admissions. A wide variety of prophylactic antiemetics, including antihistamines (e.g., hydroxyzine, promethazine), butyrophenones (e.g., droperidol), and gastrokinetic agents (e.g., metoclopramide), have been successfully used to reduce the incidence of postoperative nausea and vomiting (PONV). However, many of these antiemetics are associated with undesirable side effects.

According to an article by Tang et al. (The Effect of Timing of Ondansetron Administration on Its Efficacy, Cost-Effectiveness, and Cost-Benefit as a Prophylactic Antiemetic in the Ambulatory Setting; 1998 International Anesthesia Research Society), however, Ondansetron is effective for both the prevention and treatment of PONV without producing significant side effects. The manufacturer recommends that ondansetron be administered before induction of anesthesia when used as a prophylaxis. The recommendation is based on the hypothesis that blockade of receptors in the chemoreceptor trigger zone before the arrival of emetic stimuli associated with anesthesia and surgery provides greater antiemetic efficacy. The Tang et al. study concluded that ondansetron administered immediately before the end of surgery was the most efficacious in preventing postoperative nausea and vomiting, facilitating both early and late recovery.

Acupuncture is an ancient medical art dating back many centuries. Traditionally, points in the human body were reached by piercing the body with fine wires or needles. The needles were then rotated or manipulated about their longitudinal axes, for example by rubbing an exposed end of a needle between a thumb and finger, to stimulate the acupuncture points.

Stimulation of specific acupuncture points has been shown in several studies to have an impact in treating conditions such as nausea and vomiting, postoperative pain, headache, smoking cessation, erectile dysfunction, depression, male fertility, dysmenorrhea, and stomach acid secretion and urinary urgency. At the National Institutes of Health Consensus Conference on Acupuncture in 1997, the efficacy of acupuncture was shown in adult postoperative and chemotherapy nausea and vomiting and in postoperative dental pain, and that there were other situations, such as addiction, stroke rehabilitation, headache, menstrual cramps, tennis elbow, fibromyalgia, myofascial pain, osteoarthritis, low back pain, carpal tunnel syndrome, and asthma. Acupuncture was identified as being useful as an adjunct treatment or an acceptable alternative or be included in a comprehensive management program.

There is a recognized acupuncture point just below the crease of the inside of the wrist that has also been associated with the relief of nausea. This is one location of the median nerve whose stimulation is generally credited with producing this relief of symptoms and has been referred to as the P6 acupuncture point. In recent years, it has been observed that electrical stimulation of this location has produced the same effect (Anesthesiology 2007 December; 107(6): 903-8).

Peripheral nerve stimulators have become to be commonly used during surgery to monitor the effects of medications deployed for monitoring of neuromuscular relaxation. These devices are hand held appliances that provide a broad range of current, stimulation frequency and pattern settings. However, they tend to be costly and also lack the portability needed to attach to a patient's wrist without causing significant inconvenience. Not all peripheral nerve stimulators have the capability of continuous stimulation and many have tetanus buttons that if deployed on an awake patient would cause significant pain. These traditional nerve stimulators are not designed for continuous P6 accustimulation.

Electrical stimulation of the P6 acupuncture point, in particular, has been found to reduce the incidence of postoperative nausea and vomiting (PONV). According to the Amberger et al. study (Monitoring of Neuromuscular Blockade at the P6 Acupuncture Point Reduces the Incidence of Postoperative Nausea and Vomiting; Anesthesiology, V. 107, No. 6, December 2007) antiemetic drugs generally can reduce, but they do not eliminate postoperative nausea and vomiting (PONV). Acupuncture and its different approaches, such as needle acupuncture, electroacupuncture, and acupressure, are well described in nausea treatment. This approach is non-pharmacologic and offers the same independent efficacy as does ondansetron according to the Amberger study.

As stated, the P6 or Neiguan acupuncture point is located just proximal to the distal skin crease of the wrist, or more specifically in the anterior antebrachial region on the ulnar side of the tendon of the flexor carpi radialis. It was found that stimulation of the P6 acupuncture point in adult women undergoing gynecologic laparoscopic surgery showed a marked reduction of PONV incidence. That is, transcutaneous electrical stimulation of the P6 acupuncture point reduced nausea. Thus, Amberger et al. concluded that intraoperative P6 acupuncture point stimulation with a conventional nerve stimulator during surgery significantly reduced the incidence of PONV over 24 hours. The efficacy of P6 stimulation is similar to that of commonly used antiemetic drugs in the prevention of PONV. It is possible that using both pharmacologic and non-pharmacologic modalities may be synergistic.

Various approaches to electrostimulization in general have been considered. In one approach, there is provided a disc shaped device that has two primary layers. A first layer for adhering to a patient's skin surface and a second layer on the underside of which electrical circuitry is printed or affixed so that the electrical circuitry is sandwiched between the layers. Single use and reusable devices have further been contemplated. In the reusable device a pressure-sensitive adhesive material forms the lower layer which allows for multiple applications to a patient's skin. In either configuration, metal core insulated leads can be used for electrical connection with the opposite ends of the leads connected to jacks for connection to an impulse stimulator or can end in electrically conductive tabs.

In another approach, an electro-acupuncture device including a hydrogel for enhancing electrical conduction between the device and the skin and to provide an impedance matching layer between the device and the skin is contemplated. The hydrogel masses are sized and dimensioned so that when the pad is adapted to the device, the hydrogel masses do not bridge the electrodes to cause a short between the electrodes.

Other related devices not indicated for addressing nausea have also been described. One such approach involves an electrode-battery assembly for a miniature wireless transcutaneous electrical neuro or muscular stimulation unit capable of being removably attached. The assembly is generally comprised of two sided electrodes, batteries, various conductive transmission materials and a mechanical means for securing the conductive materials to the batteries. In addition, the assembly can be rechargeable or be disposable.

In another approach, a disposable electric bandage for electrical stimulation including a device for delivery of electric current. The device will increase circulation, generating motor and sensory stimulation and peripheral nerve stimulation. The device further includes circular electrodes and a circular power source, such as a battery. The electrodes are coated with hydrogel, which readily facilitates providing a moist surface and in addition a conductive interface means between the patch and body area of a subject. It is noted that a conductive interface may also be a conductive adhesive.

Further, yet another approach involves a self-contained electronic musculoskeletal stimulation apparatus that is a battery-operated device. The device applies electronic stimulation to a human with a stimulation protocol to introduce pain relieving electronic stimulation to the body for immediate, symptomatic relief of minor, chronic and acute musculoskeletal aches and pains and mild muscle tension. A patient attaches the apparatus onto the body with electrogel pads, which function as an adhesive to hold the apparatus in place. When the treatment button is depressed, one of the indicators will blink rapidly to indicate which intensity is currently being used to treat the patient and provide the patient with the identification of the intensity being used by the patient and an indication of treatment beginning.

Prior work has indicated, however, that existing devices are providing stimulation wave forms that are largely effective but still fail to relieve nausea and vomiting in approximately 3-5% of patients. Protocols associated with the use of the nerve stimulators have also been found lacking. Accordingly, there is need to develop a compact version of an acustimulization device that can attach comfortably to the body (i.e., wrist) so that it can be worn home and then disposed. Protocols describing the use of the device with medication are needed.

The present application addresses these and other needs. In particular, Perioperative nausea and vomiting, nausea associated with chemotherapy, nausea associated with pregnancy and nausea associated with motion. The application may be used alone or as part of a treatment regime to address nausea.

SUMMARY

Briefly and in general terms, the present disclosure is directed toward a self contained and powered unit having numerous applications both inside and outside of medicine.

In one approach, the unit embodies a compact electrokinetic nerve stimulator that is designed specifically to treat post operative nausea and vomiting with enhanced effectiveness. The disclosed device can also stimulate other nerves such as the anterior tibial nerve for the purpose of treating urinary urgency. Methods relating to the use of the stimulator are also disclosed.

In one particular aspect, the nerve stimulator is embodied in a disposable patch that is attachable to a patient's body. The patch can be sized and shaped to be placed on an exterior of a patient's skin to stimulate the median nerve. The device can include two electrodes, a microchip, a pulse generator assembly, and a power cell encapsulated by a film cover. One variation of the device contemplates a scopolamine patch attached to the device, but outside the electrical field to address both pharmacologic and nonpharmicologic modalities in a single applied device. Wireless transmission of vital signs including oxygenation and heart rate, such as through blue tooth integration is contemplated as is RF integration to transmit identification data. A method of transmitting location data through wireless transmission or RF integration or the like is also contemplated.

In one treatment modality the nerve stimulator device is activated at the beginning of surgery and permitted to operate for up to seventy-six or more hours or to the end of the battery life. A dose of ondansetron is given intravenously twenty minutes prior to the end of surgery.

In a rescue modality, general evaluation of the patient is made with history and appropriate exam, hydration status is optimized. The application of the nerve stimulator device is contemplated. A rapid acting agent with or without a longer acting agent is given intravenously. A particular approach can involve the administration of intravenous propofol and intravenous promethazine along with the use of the nerve stimulator device.

Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

Figure 1:
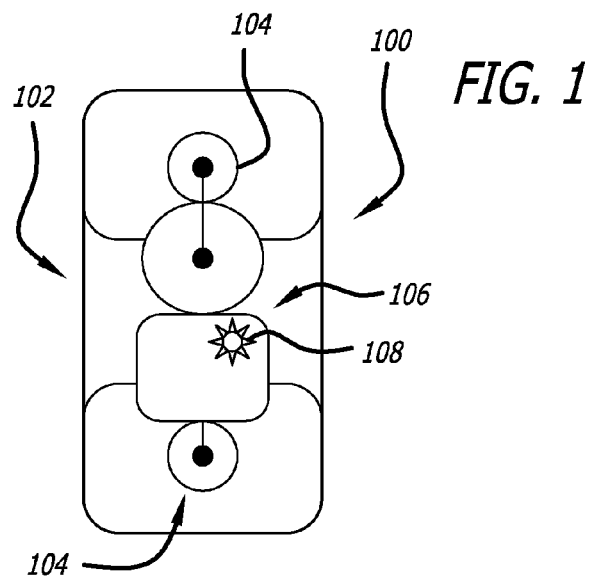
FIG. 1 is a plane view, depicting a compact electrokinetic nerve stimulator.

Referring now to the drawings, which are provided by way of example and not limitation, there is shown a compact electrokinetic stimulator.

Stimulation of the median nerve at the ventral portion of the wrist is well documented for the prevention of postoperative nausea and vomiting. Existing nerve stimulators that are employed in operating rooms to stimulate the median nerve at this location can be lacking. The problems with such apparatus are lack of uniformity among nerve stimulators, bulk of the equipment, lack of portability and disposability and cost of the equipment.

Accordingly, the present disclosure is offered as a solution to problems that hinder wider application of nerve stimulation. One application of the nerve stimulator of the present disclosure is to the anterior tibial nerve to treat urinary urgency. Other applications are also contemplated. Moreover, application of a disposable stimulator on the median nerve can facilitate the prevention of nausea in various settings such as postoperative, chemotherapy, pregnancy as well as other etiologies not otherwise specified. One contemplated location to access the median nerve is at the ventral wrist. The disposable nature of the device allows the device to travel with the patient thus preventing reactivation of the chemoreceptors trigger zone which may prevent nausea that occurs after discharge from the recovery room. It should be noted that the described treatment aids in the alleviation of the symptoms of nausea but does not treat the underlying etiology. In addition to use of the device in a preemptive protocol, the nerve stimulator may be used to treat persons experiencing postoperative nausea and vomiting or nausea from other etiologies with a rescue protocol, and may be used to stimulate nerves other than the median nerve as well.

Oscilloscopic analysis was conducted on a circuit that was being applied to the median nerve region while it was being stimulated with a 1.5 to 5 mA current. The alternating pulse and ramp functions applied by the stimulator were of low enough voltage to consider it feasible to use small battery technology as an alternative power supply. A microchip is contemplated to be sufficient to run the algorithms required to provide nerve stimulation that regulates the current to approximate a target value of 1.5 to 5 mA with a frequency of 2 Hz.

Figure 3:
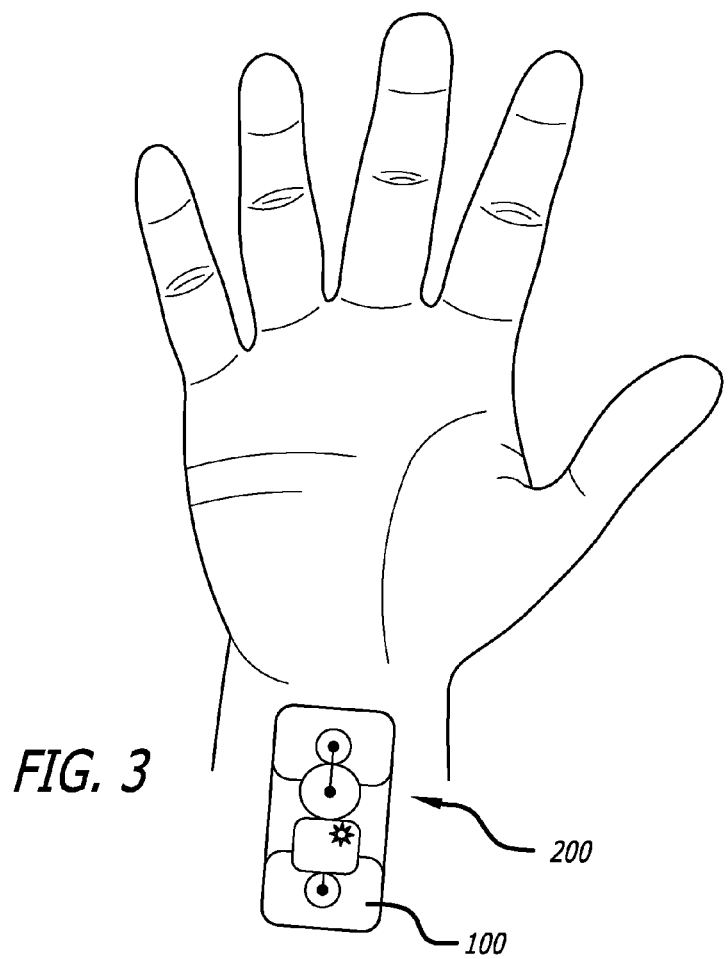
FIG. 3 is a perspective view, depicting a nerve stimulator attached to a patient.
Figure 2A:
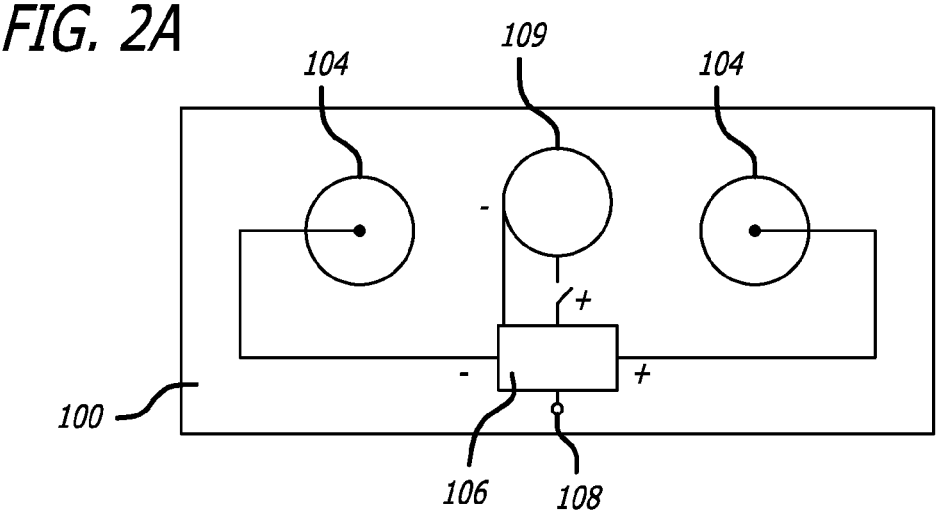
FIG. 2A is a bottom view, depicting a schematic representative of an electrokinetic nerve stimulator.

As shown in FIGS. 1-3, the nerve stimulization device 100 of the present disclosure includes a flexible plastic tape or cover 102 with two adhesive EKG style electrode assemblies 104. The nerve stimulator can act as a acustimulator device. The device can be relatively small being approximately 1.5 inches wide and about 3 inches long. A microchip and miniature circuit board 106 can be mounted between the two electrodes 104 as shown in the figures. Activation of the device 100 can be accomplished by pulling or removing a pull tab (not shown) that would complete the circuit with the power cells. A LED light 108 can be configured to flash when a current is detected. Alternatively, a magnetic wand (not shown) can be employed to start the circuit and set it to operate for either 8 or 16 hours (with a second touch of the wand, or to the end of battery life). A pulse generator powered by a battery 109 and controlled by the microchip 106 can deliver 1.5 to 5 milliamperes of current at 2 Hz. The battery 109 and microchip 106 cooperate to form a pulse generator assembly. Furthermore, this assembly can be configured to detect impedance of skin to insure that the desired amperage is delivered.

Figure 2B:
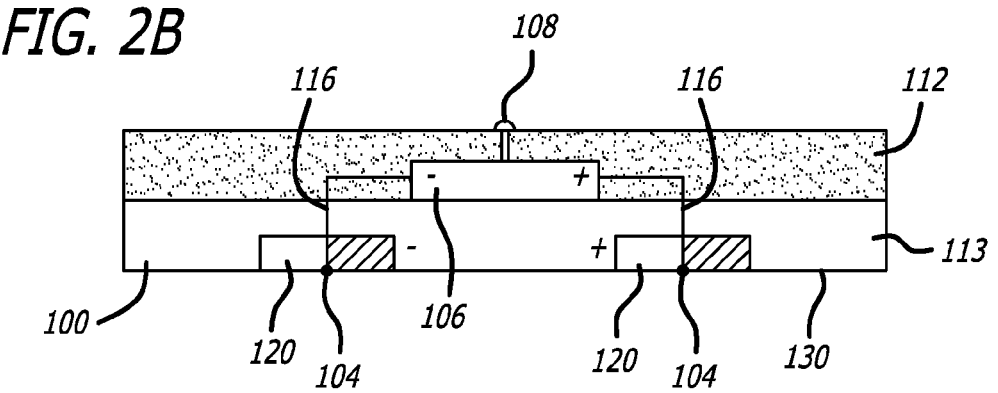
FIG. 2B is a cross-sectional view, depicting the electrokinetic nerve stimulator of FIG. 2A.
Figure 2C:
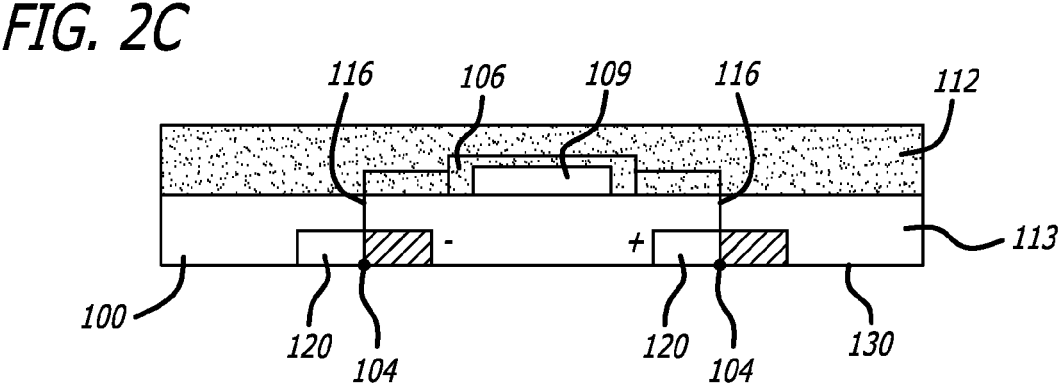
FIG. 2C is another cross-sectional side view, depicting the electrokinetic nerve stimulator of FIG. 2A.

As best seen in FIGS. 2B and 2C, a top portion 112 of the stimulator device 100 can be formed of a foam material. A bottom portion of the device is contemplated to embody a foam insulation. Wires 116 extend from the pulse generator assembly to each electrode assembly 104. Further, an energy transmitting gel 120 is associated with each electrode assembly 104 to facilitate a desired contact with the patient. An adhesive 130 can also be incorporated into the bottom surface of the device 100 for attachment to the target location on the patient's body.

Extended operation of up to 76 hours is also contemplated. Thus, a battery is chosen to provide up to or more than 76 hours of operation. Prior to assembly, the microchip 106 can be "stamped" with a control algorithm that is housed and delivered by a dedicated laptop computer.

The device 100 can be evaluated using a circuit load that simulates the impedance of the median nerve region 200. This evaluation can record the applied current and voltage wave forms and the frequency of application. Multiple rounds of evaluation can be conducted to verify circuit performance.

Use of various wave forms may provide enhanced effectiveness. One aspect is the long term use of the device following surgery. Most conventional peripheral stimulation does not last 10-20 hours. Accordingly, one contemplated approach is employing a balanced waveform that avoids the net buildup of ions (polarization). Other waveforms are contemplated to specifically avoid side effects. Yet another waveform issue for long term stimulation is the speed with which the peak current is applied to the patient. Thus, a waveform characterized by a gentle slope to this build up is also contemplated. In one embodiment, it is contemplated that the wave form that will be employed can be characterized as a box wave form at a 5 mA current and a frequency of 2 Hz.

Use of the device alone provides an estimate fifty percent reduction in postoperative nausea and vomiting. In conjunction with a single prophylactic dose of intravenous ondansetron 4 mg on emergence should offer results superior to either intervention alone. The patient continues to use the device for up to 76 hours or to end of battery life.

Elements of a rescue protocol include hydration and administration of fast acting agents capable of breaking the nausea and vomiting cycle with application of the acustimulator. In the postoperative care setting with the patient being monitored, administration of 10 mg of intravenous propofol and 6.25 to 25 mg of intravenous promethazine is performed along with the application of the acustimulator.

In one treatment protocol, a first step involves an assessment of the patient. A patient history is taken and a physical is performed. It is recognized that nausea and vomiting risk stratification is multifactored and a patient's condition must be assessed in order to arrive at the first preventative treatment. Thus, a patient's entire health and treatment history is reviewed and key aspects are noted and weighed.

Additionally, the type of procedure that the patient is about to undergo is also assessed and analyzed as is the anesthesia that will be used in the procedure. For example, it is noted whether a pelvic region or an intrabdominal procedure is to be conducted. Also surgical patients can be stratificated as to low, medium and high risk. It is to be recognized that for low risk procedures, for example minor skin procedures or radiologic procedures, an anesthetic technique that minimizes nausea such as a Total IntraVenous Anesthetic (TIVA) technique using propofol is contemplated. Moderate risk procedures such as those applicable in distal extremity orthopedic procedures would utilize the disclosed stimulation device along with a TIVA and an additional antiemetic such as Ondansetron. High risk procedures such as those associated with intra-abdominal or pelvic surgery would utilize the stimulation device, TIVA and two or more additional antiemeitics such as ondansetron and dexamethasone.

Separate specific considerations can be important where the patient is undergoing emetogenic chemotherapy. It is noted that some chemotherapeutic agents are much more emetogenic than others. As well, dosage and timing frequency and inter-patient variables can impact the probability and severity of nausea. Thus, the routine antiemetic therapy should be given and the stimulation device should be placed and activated, just before infusion of chemotherapy begins.

Moreover, distinct protocols may be necessary when treating nausea and vomiting associated with pregnancy and labor. Such patients may require a different approach due to limitations of systemic antiemetics used during pregnancy. Median nerve acustimulation is nonpharmacologic therefore avoids potential risk associated with systemic pharmacologic agents.

Treating patients suffering from motion sickness can involve other considerations. For example, it may be necessary to consider Over-the-Counter availability of motion sickness or nausea medications. Thus, a protocol combining the stimulation device with available OTC antiemetics such as Dimenhydrinate can lead to a successful treatment.

In general, the treatment of nausea, is intended to be multimodal in nature. Thus, the application of nerve stimulation in conjunction with the administration of an antiemetic is contemplated.

For a low risk patient in a method for treating nausea, the stimulization device 100 is attached to the patient at a ventral portion of the wrist above the median nerve. The device 100 is activated ideally within 60 minutes and with the patient in a supine or semi-recombinant position prior to induction of anesthesia. The device 100 is permitted to operate until depletion of the battery.

In treating a medium risk patient for nausea, the acustimulator device 100 is applied to the ventral portion of the wrist above the median nerve for example, and is activated within 60 minutes prior to the induction of the anesthesia. Again, here, the device 100 is permitted to operate until the depletion of the battery. In addition, 30 minutes prior to the emergence of anesthesia, 4 mg of Ondansetron is administered to the patient intravenously.

For a high risk patient, the acustimulator device 100 is applied as before and 4 mg of Ondansetron is administered. Additionally, 4 to 8 mg of dexamethasone is administered to the patient intravenously after the induction of anesthesia. The patient is also assessed to determine whether a scopolamine patch and/or an oral dose of aprepitant 40 mg should be given to the patient prior to induction of anesthesia.

Moreover, in the perioperative period, there are other considerations. These include maintenance of normovolemia by administration of intravenous fluids, and minimizing IV or oral opiates as these medications commonly cause nausea and regional anesthesia when appropriate. For example, utilizing peripheral nerve blocks for orthopedic procedures on the upper and lower extremities or epidural blocks for thoracic, abdominal, pelvic or lower extremity procedures can be appropriate in a treatment scheme.

Where a patient is undergoing chemotherapy, one approach to nausea treatment would be to apply the acustimulator device 100 to stimulate the median nerve 30 to 60 minutes prior to the infusion of emetogenic chemotherapy along with standard current anti-emetics. The device 100 would then be employed continuously until battery depletion.

It is also contemplated that the acustimulator device 100 can be equipped to receive replacement batteries. In this way, continued treatment for the prevention of nausea can be performed such as that might be necessary during pregnancy. The device 100 would be applied to stimulate the median nerve at early signs of pregnancy induced nausea, for example, and allowed to work until battery depletion. A new battery can then be inserted into the device 100 when new signs of nausea begin to appear after a last round of treatment.

It is further contemplated that a transdermal antiemetic such as scopolamine can be contained within the adhesive portion of the stimulation device. The antiemetic can be placed inside or outside the field of stimulation energy. In one application the drug can be delivered utilizing ionophoretic technology for transdermal delivery of anti-emetic agent(s). Other transdermal delivery technologies are contemplated. The approach of combining median nerve accustimulation and a transdermal anti-emetic in a single contained disposable unit as multimodal therapy is contemplated.

Accordingly, the present disclosure is intended to address postoperative symptoms such as nausea. Thus, it will be apparent from the foregoing that, while particular forms of the invention have been illustrated and described, various modifications can be made without parting from the spirit and scope of the invention.

I claim:

1. A system for treating post-operative nausea in a patient, comprising:
 a nerve stimulator having a housing with an upper surface and a lower surface, the lower surface including an adhesive, a pulse generator disposed within the housing and the pulse generator including a battery which drives a microchip, and a pair of electrodes disposed on the lower surface of the housing and in communication with the pulse generator, the housing of the nerve stimulator configured to be applied to a patient prior or during a surgical procedure and to remain with a patient after the patient leaves a treatment facility therefore avoiding reactivation of the chemoreceptor trigger zone that could result in nausea; and a preemptive protocol for treating nausea.

2. The system of claim 1, wherein the battery drives the microchip and a circuit communicator with the pair of electrodes.

3. The system of claim 1, wherein the signal is a box wave form at between 1.5 to 5 mA current and a frequency of 2 Hz.

4. The system of claim 3, wherein the battery has a life of 76 hours or more.

5. The system of claim 1, further comprising an insulating matrix material.

6. The system of claim 1, wherein the pulse generator is mounted between the pair of electrodes.

7. The system of claim 1, further comprising a transdermal antiemetic.

8. The system of claim 1, wherein the nerve stimulator is configured to provide a gentle build up to peak current.

9. The system of claim 1, wherein the housing of the nerve stimulator is about 1.5 inches wide and about 3 inches long.

* * * * *